United States Patent
Kopalidis et al.

(10) Patent No.: US 8,653,807 B2
(45) Date of Patent: Feb. 18, 2014

(54) APPARATUS AND METHOD FOR MEASURING ION BEAM CURRENT

(75) Inventors: Peter M Kopalidis, Fremont, CA (US); Zhimin Wan, Sunnyvale, CA (US)

(73) Assignee: Advanced Ion Beam Technology, Inc., San Jose, CA (US)

( * ) Notice: Subject to any disclaimer, the term of this patent is extended or adjusted under 35 U.S.C. 154(b) by 863 days.

(21) Appl. No.: 12/841,833

(22) Filed: Jul. 22, 2010

(65) Prior Publication Data

US 2012/0019257 A1 Jan. 26, 2012

(51) Int. Cl.
  *G01N 27/00* (2006.01)
  *G01N 27/62* (2006.01)
  *H01J 37/08* (2006.01)
  *A61N 5/00* (2006.01)

(52) U.S. Cl.
  USPC ............... 324/71.3; 324/459; 250/492.21; 250/492.3

(58) Field of Classification Search
  USPC .......... 324/459, 71.3, 71.1, 76.11; 250/492.1, 250/492.2, 492.21, 492.3, 397, 423 R, 427
  See application file for complete search history.

(56) References Cited

U.S. PATENT DOCUMENTS

| | | | |
|---|---|---|---|
| 6,723,998 B2 * | 4/2004 | Bisson et al. | 250/397 |
| 8,040,124 B2 * | 10/2011 | Berrian et al. | 324/76.11 |
| 2003/0222227 A1 | 12/2003 | Richards et al. | |
| 2008/0251737 A1 * | 10/2008 | Tsukihara et al. | 250/492.21 |

* cited by examiner

*Primary Examiner* — Hoai-An D Nguyen
(74) *Attorney, Agent, or Firm* — Stout, Uxa, Buyan & Mullins, LLP

(57) ABSTRACT

Techniques for ion beam current measurement, especially for measuring low energy ion beam current, are disclosed. In one exemplary embodiment, the techniques may be realized as an ion beam current measurement apparatus has at least a planar Faraday cup and a magnet device. The planar Faraday cup is close to an inner surface of a chamber wall, and may be non-parallel to or parallel to the inner surface. The magnet device is located close to the planar Faraday cup. Therefore, by properly adjusting the magnetic field, secondary electrons, incoming electrons and low energy ions may be adequately suppressed. Further, the planar Faraday cup may surround an opening of an additional Faraday cup being any conventional Faraday cup. Therefore, the whole ion beam may be received and measured well by the larger cross-section area of at least the planar Faraday cup on the ion beam path.

18 Claims, 9 Drawing Sheets

401 — Prepare an ion beam current measurement apparatus in an ion implanter. The ion beam current measurement apparatus has at least a planar Faraday cup and a magnet device, and may have an optional additional Faraday cup. Herein, the planar Faraday cup is located close to an inner surface of a chamber wall and faces an inner space of the chamber, the magnet device is located close to the planar Faraday cup, and the optional additional Faraday cup may be any conventional Faraday cup.

402 — Monitor an ion beam current received by the planar Faraday cup, even received by the optional additional Faraday cup.

FIG. 4

APPARATUS AND METHOD FOR MEASURING ION BEAM CURRENT

BACKGROUND OF THE INVENTION

1. Field of the Invention

The present disclosure relates generally to ion implantation and more particularly to techniques for measuring ion beam current.

2. Background of Related Art

Ion implanters are commonly used in the production of semiconductor devices, flat panels and solar cells. An ion source is used to generate a charged ion beam, which is then analyzed by a mass analyzer to remove ions with undesired charge-to-mass ratios and then directed toward a workpiece, such as a semiconductor wafer or a glass plate, held by a holder. One or more devices may be located between the mass analyzer and the holder for adjusting the ion beam by applying an electric field, a magnetic field and/or other approach. These devices, such as collimator and acceleration/deceleration electrodes, are usually viewed as a portion of the "beam optics". To monitor the ion beam current, which is significantly related to the dosage in the implanted workpiece, a Faraday cup is commonly used to receive and measure the ion beam. Usually the Faraday cup is a deep structure that extends into a chamber wall and has an opening that faces a workpiece position where a workpiece held by the holder is located. By moving one or more of the holder and the ion beam, the ion beam may be directed toward the Faraday cup for measuring the ion beam current.

FIG. 1 is a representative schematic diagram of the configuration of the conventional Faraday cup. An ion beam 12 from the mass analyzer (not shown) is directed from the left side of a chamber 11 to a Faraday cup 13, which is located on the right side of the chamber 11 and is a deep structure that extends into a chamber wall of the chamber 11. The Faraday cup 13 has an opening facing an inner space of the chamber 11, such as a workpiece position where a workpiece to be implanted is located. Clearly, when the ion beam 12 is projected into the Faraday cup 13, the charges of these ions in the ion beam 12 will be measured by the current meter 14 electrically coupled with the Faraday cup 13. In addition, a separate set of magnets may be located close to the Faraday cup 13 for adequately suppressing secondary electrons, incoming electrons and low energy ions, so that the current measured by the current meter 14 is accurately equal to the current of the charges delivered by the ion beam 12.

However, there are some practical problems. First, the ion beam 12 from the mass analyzer, or through the beam optics, may be misaligned. Then, the ion beam 12 may be not totally projected into the Faraday cup 13. Second, owing to space charge effects, the expansion of the ion beam 12 is inevitable. The beam expansion is more serious for a low energy ion beam, because the slower ion velocity results in longer travel time from the mass analyzer to the Faraday cup 13. Then, especially for the low energy ion beam, the ion beam 12 tends to be tall and wide and a significant percentage of the total beam current is at the edges. Hence, when the ion beam 12 may not be totally projected into the Faraday cup 13, the ratio of lost ion beam current will be more serious. Third, with the popularity of larger-size workpieces, such as 12-inch wafers, there is a tendency toward taller ion beams. Clearly, when the size of the entrance of the Faraday cup 13 is limited, the taller beams present a risk of projecting part of the ion beam 12 outside the Faraday cup 13.

In short, the Faraday cup 13 may only measure part of the ion beam 12, and this reduces the accuracy of dosimetry control.

A popular approach to achieve accurate dose control is to use a profiler to measure the ion beam 12. Hence, by using the acquired beam current distribution of the ion beam 12, the current measured by the Faraday cup 13 may be corrected. However, the hardware cost and the operation of the profiler will increase the total cost and decrease the throughput. Another approach is directly increasing the size of the entrance of the Faraday cup 13 for increasing the cross-section area capable of receiving the ion beam. However, much hardware exists on the outside chamber wall of the chamber 11. For example, the gas pipeline connected to the vacuum pump for pumping, the power line for powering the beam optics or the devices for moving the holder, and the window for moving the workpiece in and out the chamber 11. Hence, the size of the conventional Faraday cup, especially the size of the opening of the conventional Faraday cup, cannot be arbitrarily enlarged.

Accordingly, a novel and efficient approach for the above issue is desired.

SUMMARY OF THE INVENTION

In order to solve the foregoing problems, this invention proposes a method and an apparatus for accurately measuring the ion beam current.

One exemplary embodiment is an ion beam current measurement apparatus having at least a planar Faraday cup and a magnet device. The planar Faraday cup is located close to an inner surface of a chamber wall, and may be a plate-like structure non-parallel to or parallel to the inner surface. The magnet device is located close to the planar Faraday cup. Therefore, by properly adjusting the magnet field applied by the magnet device around the planar Faraday cup, all of secondary electrons, incoming electrons and low energy ions may be adequately suppressed. Optionally, the planar Faraday cup may surround an opening of an additional Faraday cup which may be any conventional Faraday cup. Therefore, the whole ion beam may be received and measured owing to at least the larger cross-section area of the planar Faraday cup on the ion beam path.

Another exemplary embodiment is a method for measuring the ion beam current. Initially, prepare an ion beam current measurement apparatus in an ion implanter. As disclosed above, the ion beam current measurement apparatus has at least a planar Faraday cup and a magnet device, and may further have an additional Faraday cup. Then, monitor the ion beam current received by the planar Faraday cup, even by the additional Faraday cup. Of course, the method may further adjust the magnet device for generating different magnetic fields being suitable for measuring different ion beams having different sizes, different shapes or other different characteristics.

The foregoing and other features of the invention will be apparent from the following more detailed description of embodiments of the invention.

BRIEF DESCRIPTION OF THE DRAWINGS

FIG. 4 is a flowchart of a method according to another embodiment of the invention.

DETAILED DESCRIPTION OF THE INVENTION

The detailed description of the present invention will be discussed in the following embodiments, which are not intended to limit the scope of the present invention, but can be adapted for other application. While drawings are illustrated with some details, it is appreciated that the quantity of the disclosed components may be greater or less than that disclosed, except where expressly restricting the amount of the components.

One main disadvantage of the conventional techniques is that the limited cross-section area of the conventional Faraday cup on a plane tilt to, or vertical to, the ion beam path. Hence, partial ion beam may be not received and measured by the conventional Faraday cup, especially when the deflect angle and/or the beam height of the ion beam is larger. Another main disadvantage of the conventional techniques is that the usage of the profiler results in inevitably an extra device (profiler) and an extra step (measuring ion beam by the profiler and using the measured result to modify the measured result of the Faraday cup). Moreover, the profiler may be not close enough to the entrance of the opening of the Faraday cup, so that the correctness of the modification is decreased. Accordingly, the conventional techniques cannot balance the requirements of accuracy and efficiency well.

One starting point of the invention is to directly receive and measure whole the ion beam, i.e., to directly use the Faraday cup. In other words, the profiler is only an option at most for measuring the ion beam current distribution or other messages related to the ion beam. However, as briefly described above, the size of the opening of the conventional Faraday cup usually is finite and has a clear upper limitation due to the practical design requirements of the chamber (or chamber wall). Therefore, the invention proposes a novel design of the Faraday cup (or viewed as a novel ion beam current measurement apparatus). Moreover, to ensure only the required ions are measured, the proposed ion beam current measurement apparatus should be able to suppress at least slow ions, secondary electrons and incoming electrons within the ion beam for minimizing the error on the measured ion beam current.

Figure 1:
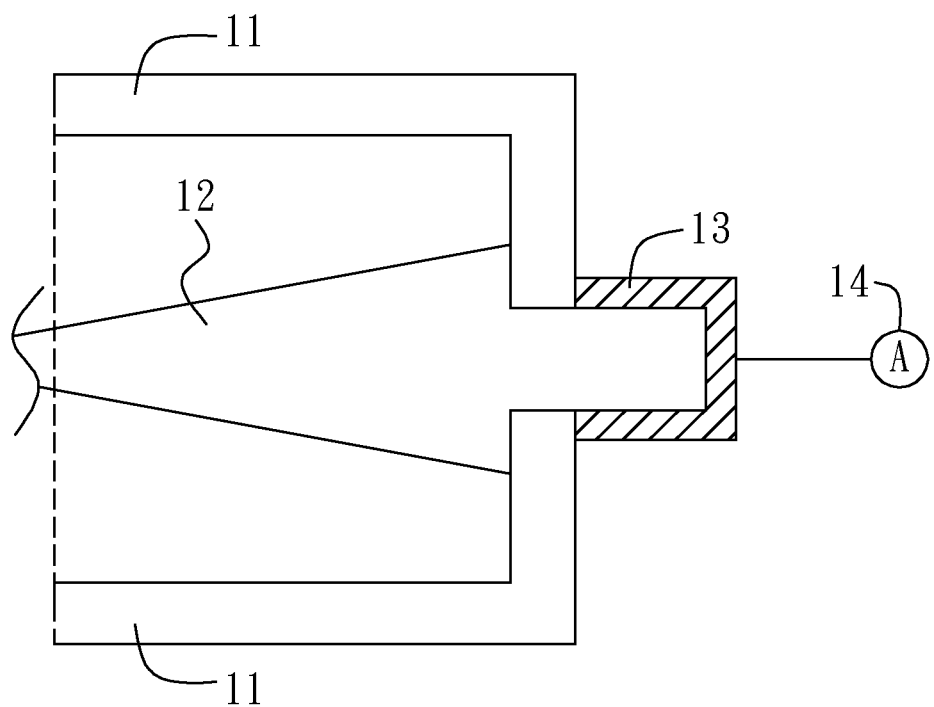
FIG. 1 is a representative schematic diagram of the configuration of the conventional Faraday cup.
Figure 2A:
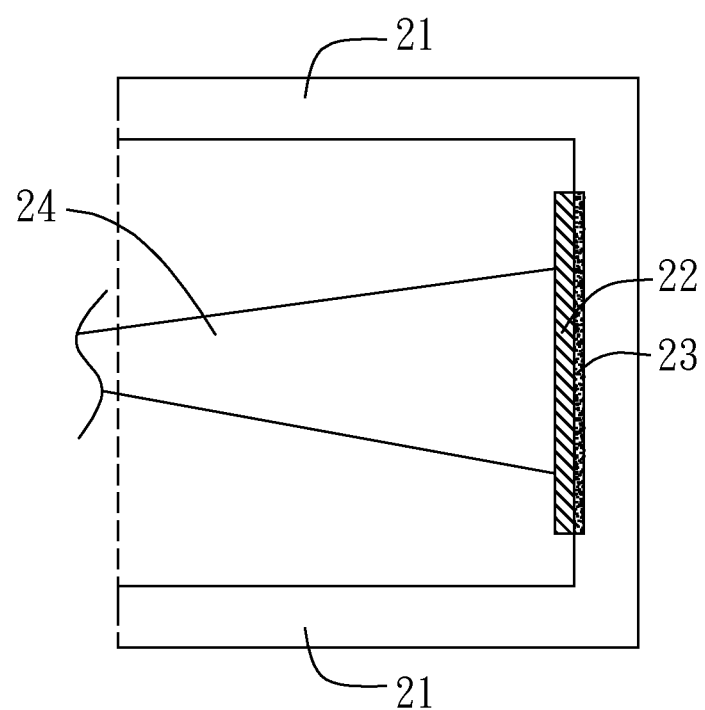
FIG. 2A and FIG. 2B are two representative schematic diagrams of one proposed ion beam current measurement apparatus according to one embodiment of the invention.
Figure 2B:
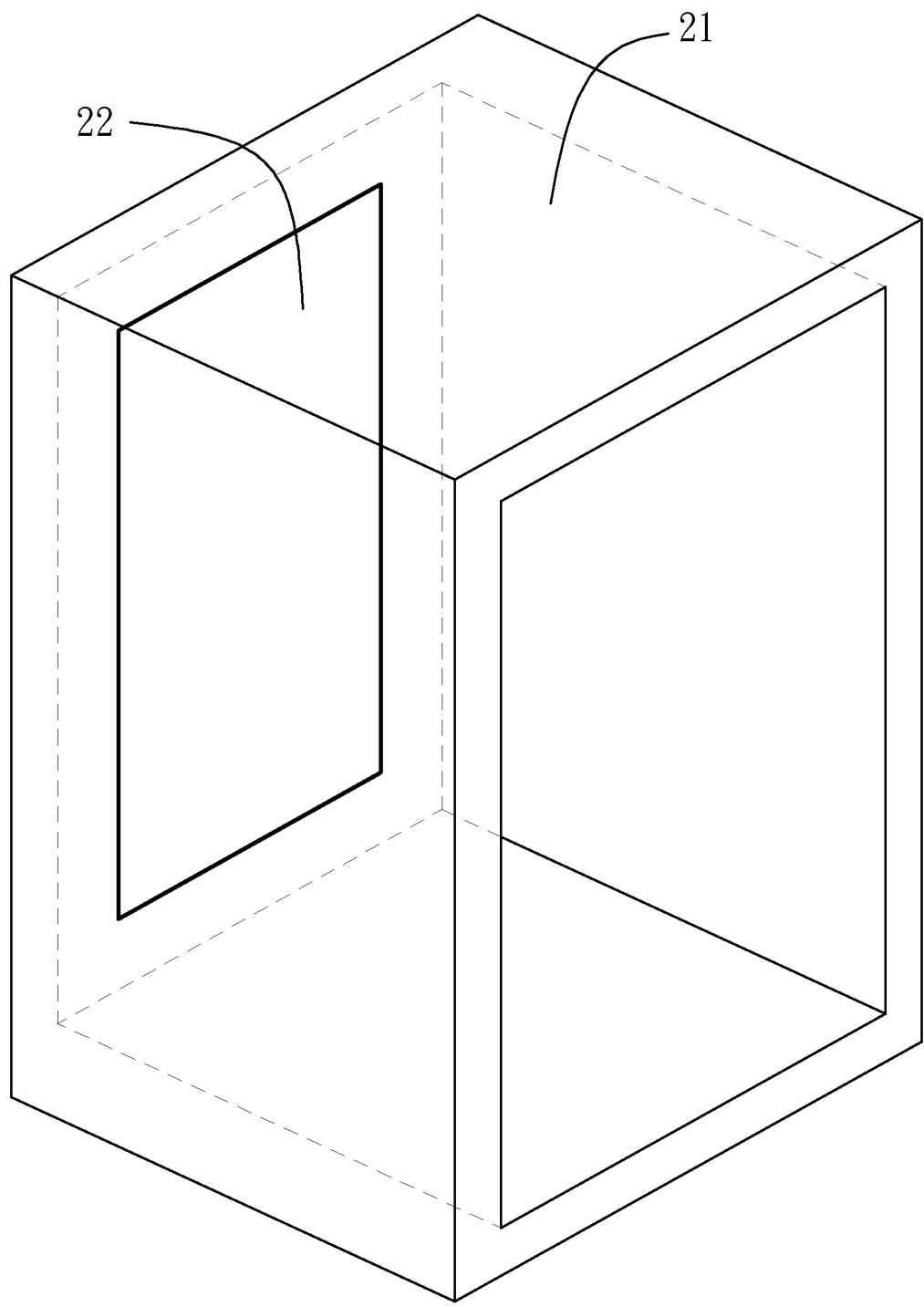

One embodiment is an ion beam current measurement apparatus with two representative schematic diagrams, FIG. 2A and FIG. 2B. The proposed ion beam current measurement apparatus is located close to a portion of a chamber wall of a chamber 21. An ion beam 24 is directed to implant a workpiece when the workpiece is located inside the chamber 21. The workpiece may be a wafer, a semiconductor plate, a glass plate or any plate whose surface quality may be changed by implanted ions. The proposed ion beam current measurement apparatus has at least a planar Faraday cup 22 and a magnet device 23. In short, the planar Faraday cup 22 is close to an inner surface of the chamber wall, and faces the inner space of the chamber 21. Further, the magnet device 23 is located close to the planar Faraday cup 22 for applying proper magnetic field around the planar Faraday cup 22.

Reasonably, the planar Faraday cup 22 is essentially positioned on a plane across the ion beam path. For example, when the ion beam path is vertical to the inner surface of the chamber wall, the planar Faraday cup 22 may be positioned on the inner surface of the chamber wall or may be a three dimensional structure around the intersection between the ion beam path and the chamber wall. In other words, the planar Faraday cup 22 may have non-zero angle with respect to the chamber wall, or the planar Faraday cup 22 may be at least essentially parallel to, even absolutely parallel to, the inner surface of the chamber wall. Accordingly, the cross-section area of the ion beam current measurement apparatus on the ion beam path is significantly increased. Particularly, most of hardware is located outside the chamber (or attached on the outer surface of the chamber wall) for minimizing potential contamination inside the chamber. Therefore, the planar Faraday cup inside the chamber usually may be extended with less limitation (less risk of being overlapped and/or blocked with other hardware inside the chamber.) Accordingly, the available surface size limitation on the planar Faraday may be significantly larger than the limitation on the opening of the conventional Faraday cup. Hence, the ion beam 24 may be totally received by the planar Faraday cup, no matter the deflect angle and/or the beam height of the ion beam is larger.

The planar Faraday cup 22 usually is configured according to at least one of the following requirements: (a) covers an entire area around the intersection between the ion beam current direction and the chamber wall without any gap; and (b) extended along direction across the ion beam path with an extended distance being inversely proportional to a predetermined limitation of an ion beam energy. The former requirement is used to avoid the loss of at least a portion of a continuous ion beam (not received and measured), especially the middle portion of the ion beam. The latter requirement is used to avoid the loss of at least a portion of an ion beam with larger deflected angle and/or longer beam height, especially the two terminal portions of the ion beam.

Figure 2C:
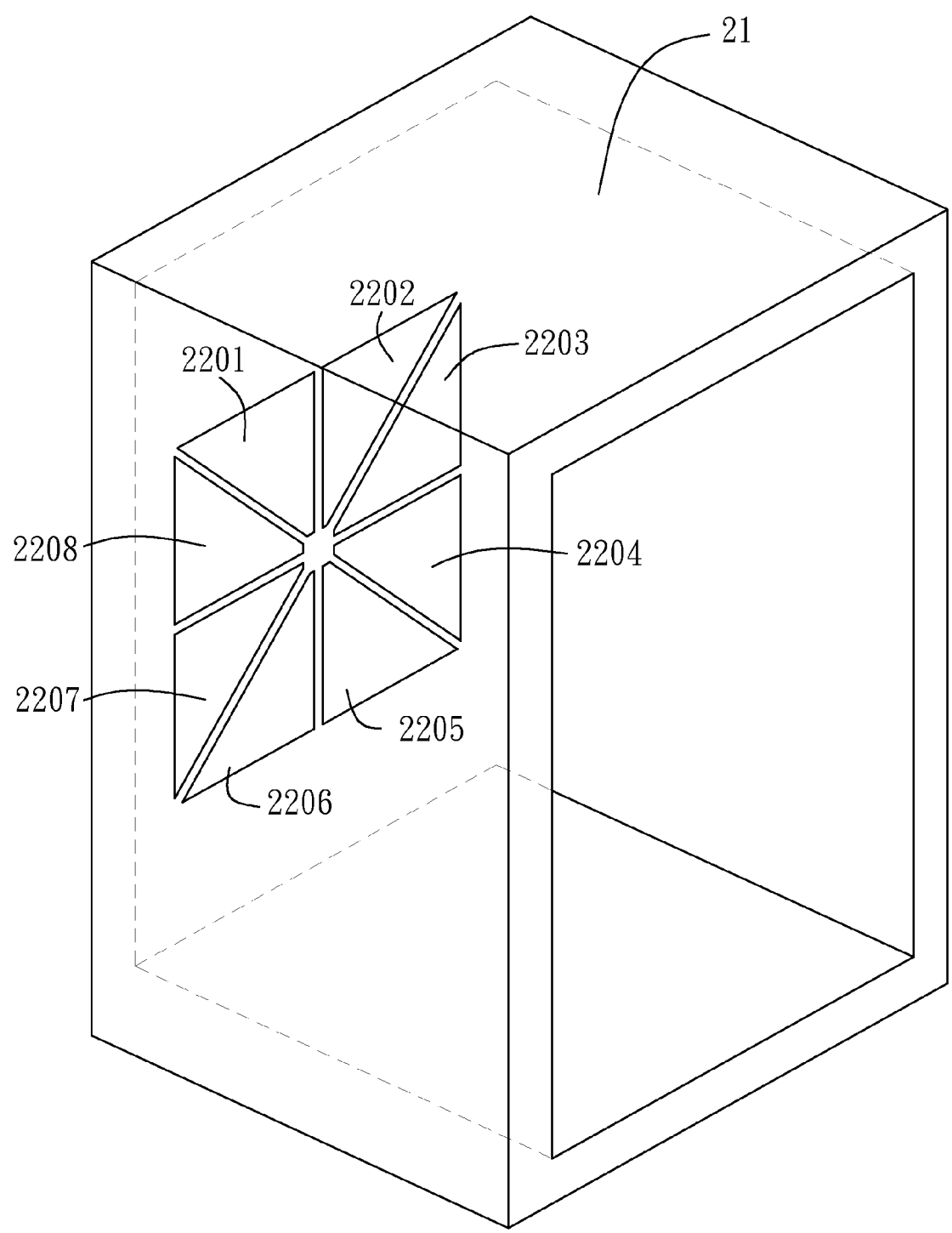
FIG. 2C is a representative schematic diagram of one proposed planar Faraday cup according to another embodiment of the invention.
Figure 2D:
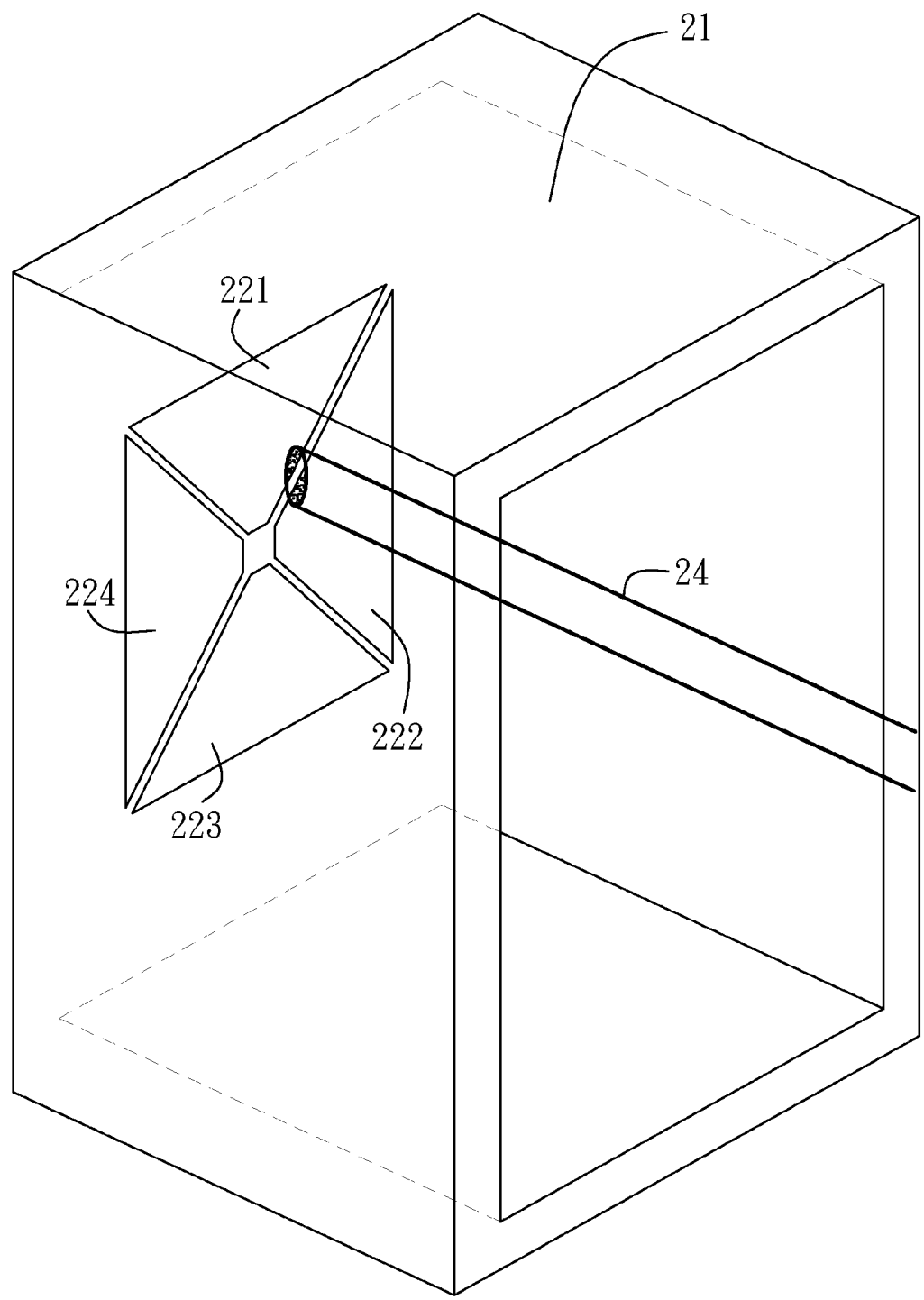
FIG. 2D is a representative schematic diagram of one proposed ion beam current measurement apparatus according to another embodiment of the invention.

Note that the details of how to configure the planar Faraday cup 22 are not limited. Different embodiments may have different variations. For example, to properly receive and measure the charged ions in the ion beam, the planar Faraday cup may be consisted of one or more conductive plates. As shown in FIG. 2C, the planar Faraday cup 22 has eight long/wide conductive plates 2201-2208. Herein, each conductive plate is electrically insulated with other conductive plates. Hence, by separately measure the individual ion beam current appeared on different conductive plates, how the ion beam 24 is deflected and/or dispersed may be properly monitored. For example, in the case shown in FIG. 2D, when the ion beam 24 is essentially projected onto the top and right corners of the ion beam current measurement device, the individual ion beam current is highest on the top conductive plate 221, middle on the right conductive plate 222, and zero on the left and bottom conductive plates 223/224. Hence, in addition to the total ion beam current measurement, the embodiment can also acquire information on the beam position by separating the four conductive plates 221/222/223/224 so that instant signals may be provided to control the beam position and the beam angle during automatic ion beam tuning. Reasonably, when the ion beam current measurement apparatus is formed by one and only one conductive plate may, only the total amount of ion beam current may be measured. But, when the ion beam current measurement apparatus is formed by two or more conductive plates, how the total amount of the ion beam current is distributed (or extend) on a plane crossing the ion beam path may be measured. In other non-illustrated embodiments, the number, the shape, the size and the position (even other parameters) of these conductive plates are adjustable.

Of course, to meet the above requirement (a), the area occupied by the electrical insulator used to separate electrically different conductive plates should be minimized. Moreover, to minimize potential contamination induced by the collision between the ion beam (or any particle) and the conductive plates, the material of a surface of the planar Faraday cup 22 usually is graphite. But, it also may be conductive glue, conductive film, and so on.

On the other hand, the magnet device 23 is designed to generate a magnetic field for containing the undesired charged particles, such as the slow ions and all kinds of electrons. The generated magnetic field is used to minimize the chance that the undesired charged particles collide with the planar Faraday cup 22 and then becomes a portion of the measured ion beam current. The generated magnetic field also is used to minimize the chance that the undesired charged particles come into the inner space and then may react with the workpiece to be implanted. Therefore, the magnetic field should be parallel to the surface of the planar Faraday cup 22 at least in a section near the intersection between the ion beam path and the planar Faraday cup 22, so that these undesired charged particles rotate around the magnetic flux and then will not be received and measured by the planar Faraday cup. Herein, whether the generated magnetic field becomes perpendicular to the planar Faraday cup 22 about a specific distance away from the intersection (i.e., about out the section) between the ion beam path and the chamber wall is optional. Also, the specific distance is a variable parameter.

Reasonably, to form a magnetic field parallel to a planar structure, the magnet device 23 is formed generally by one or more thin magnets placed below the planar Faraday cup 22. For example, the thin magnet located between the planar Faraday cup 22 and the chamber wall, or the thin magnet(s) embedded into the chamber wall. Moreover, when the planar Faraday cup 22 has one or more conductive plates, the magnet device may also have one or more thin magnets that each thin magnet is located under a conductive plate in a one-on-one relation. However, other types of magnetic field source also are acceptable. For example, the coils disposed along the rods that parallel to the planar Faraday cup 22 and positioned inside the chamber wall.

Furthermore, except to properly configure the magnet device 23 for adjusting the distribution of the generated magnetic field, the power inputted into the magnet device also may be properly adjusted for adjusting the amplitude of the generated magnetic field. Hence, because the mass of electron is significantly less than the mass of ion and the velocity of a slow ion is significantly less than the velocity of the desired ions, it is potential and practical to have a magnetic field with the distribution disclosed above and an amplitude larger than a threshold amplitude. Therefore, only the desired ions are not suppressed and are received/measured. In contrast, all electrons within the ion beam, all secondary electrons generated by the interaction between ions and implanted surface, and all slow ions generated by the collision between the desired ions (or other slow ions) may be suppressed.

In addition, although not shown in any figure and any described embodiment, one or more current meters may be electrically connected to the conductive plates in a one-on-one relation, so that the ion beam may be precisely and flexibly measured.

Besides, the proposed planer Faraday cup 22 and the magnet device 23 may be integrated with the conventional Faraday cup. In such situation, the structure of the chamber may be only amended slightly to add the planar Faraday 22 and the magnet device 23 in the inner portion of the chamber 21. Generally, the conventional Faraday cup is a deep structure extending into the chamber wall and having an opening that faces the inner space of the chamber. Hence, all above embodiments may be modified slightly to include an optional additional Faraday cup, i.e., the conventional Faraday cup. In this situation, the planar Faraday cup surrounds the opening of the additional Faraday cup. In other words, all above embodiments may be amended simply by replacing the above described "the intersection between the planer Faraday cup and the ion beam path" by the opening of the additional Faraday cup.

Figure 3A:
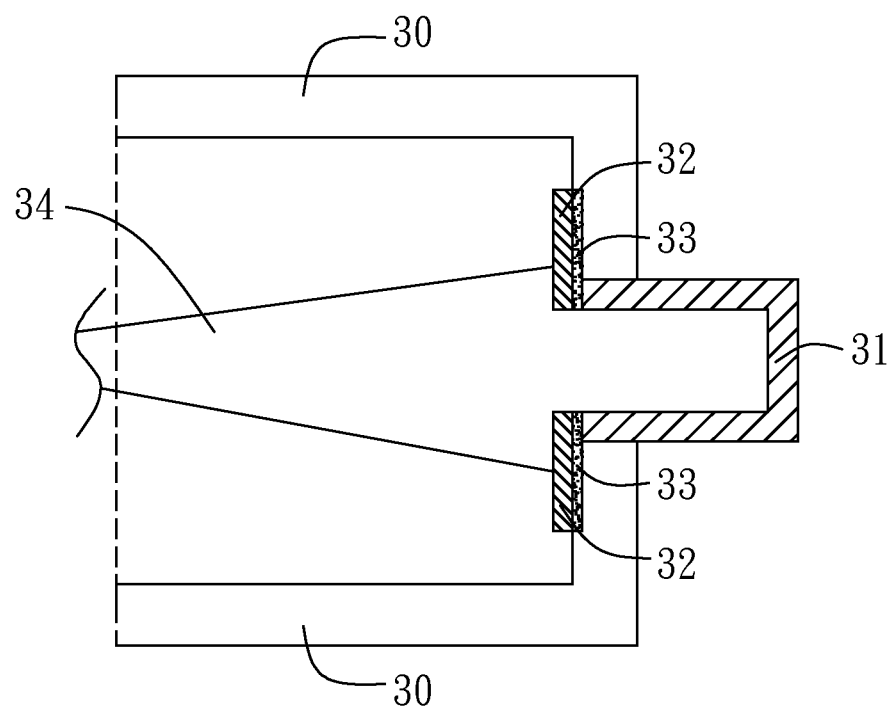
FIG. 3A and FIG. 3B are two representative schematic diagrams of one proposed ion beam current measurement apparatus according to another embodiment of the invention.
Figure 3B:
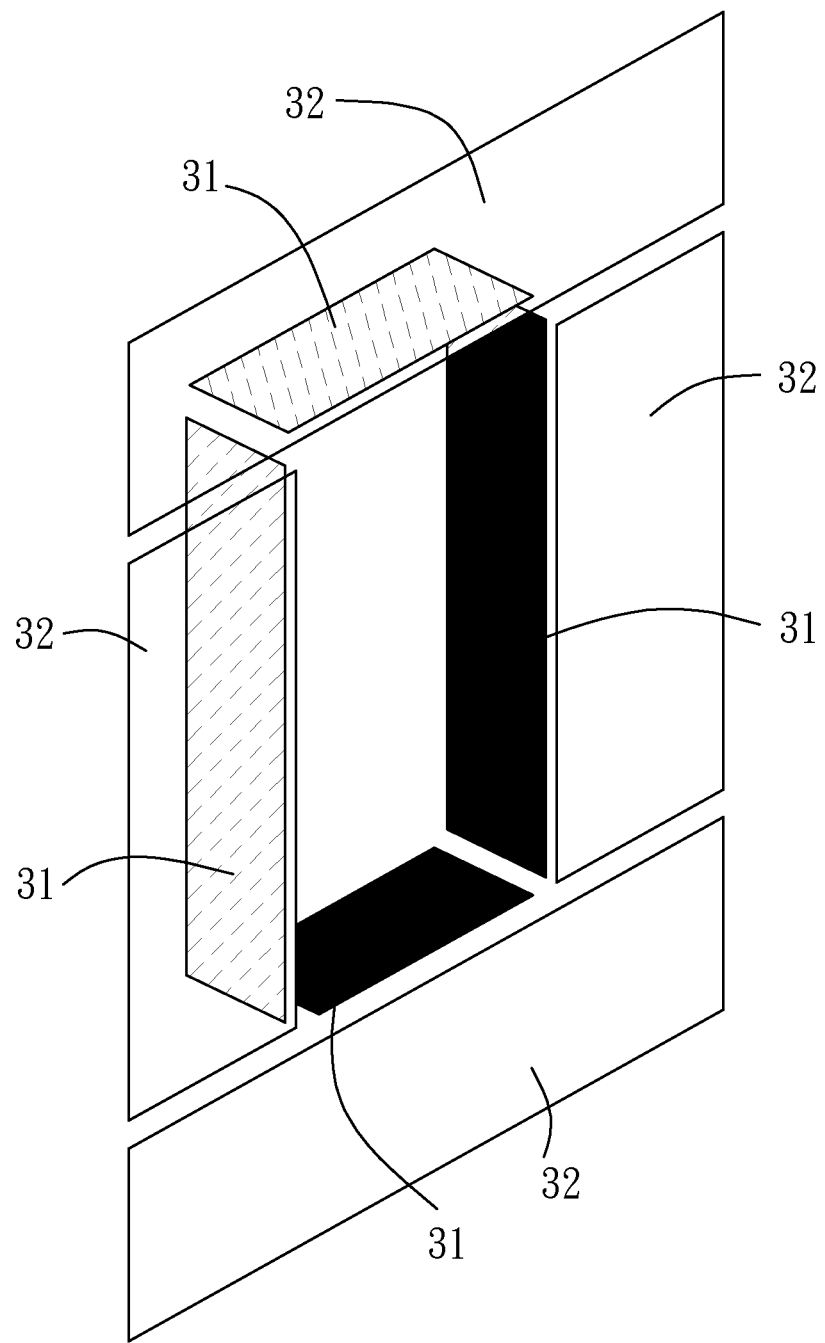

One such embodiment is an ion beam current measurement apparatus with two representative schematic diagrams, FIG. 3A and FIG. 3B. The proposed ion beam current measurement apparatus is located on a portion of a chamber wall of a chamber 30 where an ion beam 34 is directed to implant a workpiece when the workpiece is located inside the chamber 30. The proposed ion beam current measurement apparatus has at least an additional Faraday cup 31, a planar Faraday cup 32 and a magnet device 33. In short, the additional Faraday cup 31 is a deep structure that extends into the chamber wall and has an opening that faces an inner space of the chamber 30. More details of the additional Faraday cup 31 are omitted herein, because the additional Faraday cup 31 may be any conventional Faraday cup. Besides, the planar Faraday cup 32 surrounds the opening and faces the inner space, and may be tilt to, essentially parallel to or absolutely parallel to an inner surface of the chamber wall. Moreover the magnet device 33 is located close to the planar Faraday cup 32 for applying proper magnetic field around the planar Faraday cup 32.

As shown in FIG. 3A and FIG. 3B, the planar Faraday cup 32 may significantly increase the cross-section of the ion beam current measurement apparatus for receiving the ion beam 34. Hence, to compare with the conventional Faraday cup, such embodiments may significantly increase the possibility of measuring correctly the ion beam current. Note that the details of how the planar Faraday cup 22 is configured are not limited. Different embodiments may have different variations. For example, when the size of the opening is larger, the extended distance of the planar Faraday cup 32 may be shorter for similar ion beams 24 with similar ion beam conditions (similar ion beam energy or similar deflected angle). For example, when the size of the opening is fixed, the extended distance of the planer Faraday cup 22 may be larger for ion beam 24 with lower ion beam energy or longer beam height. For example, when the beam height of the ion beam 24 is along a Y-axis and the ion beam is delivered along a Z-axis, the required extended distance of the planar Faraday cup 22 may be longer along the Y-axis but shorter along an X-axis. For example, the proposed ion beam current measurement apparatus may be divided into two or more individual conductive plates. Hence, not only the total current of the ion beam may be precisely measured, but also both the size and the direction of the ion beam may be efficiently measured.

Figure 3C:
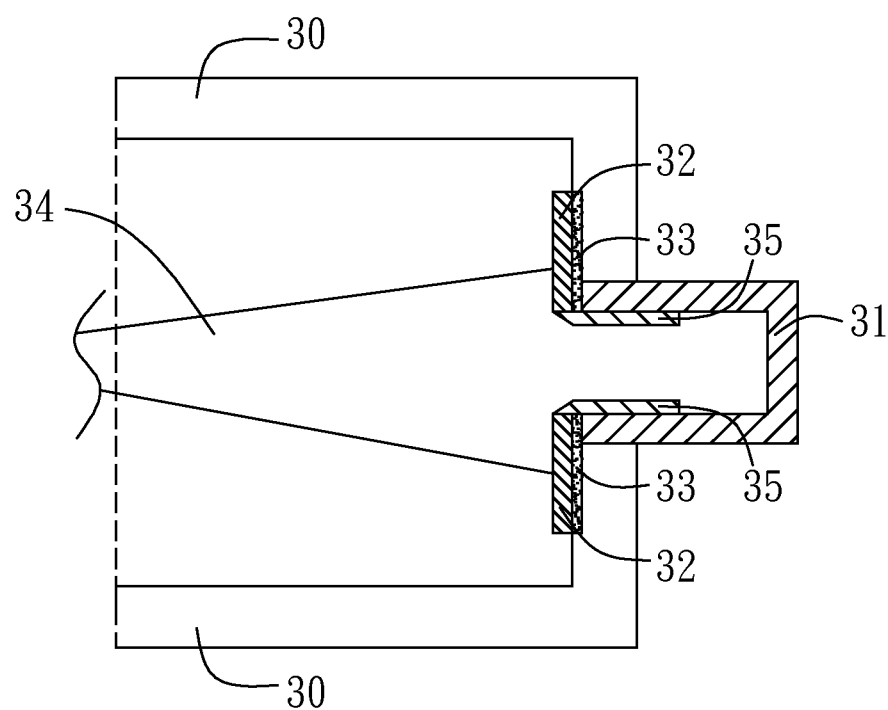
FIG. 3C is a representative schematic diagram of the proposed planar Faraday cup, the proposed additional Faraday cup and the proposed additional conductive plates according to another embodiment of the invention.

Furthermore, to more flexibly and precisely measure the ion beam current, one more embodiment, as shown in FIG. 3C, has one or more additional conductive plates 35 perpendicular to the planar Faraday cup 32 at the entrance of the opening. Herein, the additional conductive plates 35 are electrically floating and electrically connected to the planar Faraday cup 32, and may be graphite plates or other equivalent plates made by conductive material(s). Therefore, the current generated by charged particles received by the additional conductive plates 35 are incorporated with the current received by the planar Faraday cup 32. Accordingly, the proposed ion beam current measurement apparatus may receive and measure the ion beam current with more correctness and flexibility.

Of course, to monitor the distribution of the ion beam as discussed above, when the planar Faraday cup 32 is consisting of one or more conductive plates, the additional conductive plates 35 and the conductive plates are corresponded in a one-on-one relation. Moreover, the magnet device 33 may be located between the additional conductive plates 35 and the chamber wall, so that the additional conductive plates 35 may only receive the desired ions. The requirement of the generated magnetic field is similar with the conditions discussed above and thus are omitted herein.

One main advantage of these proposed ion beam current measurement apparatuses is the larger cross-section for receiving the ion beam. Usually, the hardware on the inner surface of the chamber wall is significantly less than the hardware on the outer surface of the chamber wall. Hence, the upper limitation of the size of the planar Faraday cup may be less restricted, i.e., the size of the planar Faraday cup may be significantly larger than the size of the opening of the conventional Faraday cup (i.e., the size of the opening of the additional Faraday cup.) Therefore, the proposed ion beam current measurement apparatus may receive and measure whole ion beam, no matter how the ion beam is deflected and/or dispersed or how the ion beam is distributed. Accordingly, it is possible and practical to only use the proposed ion beam current measurement apparatus without using the profiler for further amendment.

Another main advantage of these proposed ion beam current measurement apparatuses is the thin thickness. Both the planar Faraday cup and the magnet device may be plate-like structures (conductive plates and thin magnets) so that the thickness of partial proposed ion beam measured apparatus in the inner space of the chamber wall may be reduced. Also, the optional additional Faraday cup is not located inside the inner space of the chamber but is in the chamber wall of the chamber (even on the outer space of the chamber). Hence, the net thickness of the proposed ion beam current measurement apparatus in the inner space of the chamber may be effectively reduced, and then the proposed ion beam current measurement apparatuses may be attached suitably on the chamber wall without any modification on the chamber wall. Furthermore, the plate-like structures of the planar Faraday cup and the magnet device allow the workpiece being located close to the planar Faraday cup (i.e., located close to the opening of the additional Faraday cup), so that the correctness of the ion beam current measurement may be further improved.

One more embodiment, as shown in FIG. 4, is a method for measuring ion beam current. Initially, as shown in block 401, prepare an ion beam current measurement apparatus in an ion implanter. The ion beam current measurement apparatus has at least a planar Faraday cup and a magnet device, and may have an optional additional Faraday cup. Herein, the planar Faraday cup is located close to an inner surface of a chamber wall and faces an inner space of the chamber, the magnet device is located close to the planar Faraday cup, and the optional additional Faraday cup may be any conventional Faraday cup. Then, as shown in block 402, monitor an ion beam current received by the planar Faraday cup, even received by the optional additional Faraday cup.

Reasonably, the flowchart shown in FIG. 4 is the basic operation of the ion beam measurement apparatus proposed above. Initially, prepare and turn on an ion implanter with such ion beam current measurement apparatus, and then measure the ion beam current appeared on whole the ion beam current measurement apparatus. However, different implantations may require different ion beams. For example, to form the N-type wall of the P-type transistors may require high energy ion beam, but to form the shallow junction may require low energy ion beam. Therefore, to properly suppress only the un-desired charge particles, an optional step is adjusting the magnetic field generated by the magnet device during an operation period of the ion implanter. Herein, the amplitude of the magnetic field may be adjusted by adjusting the power used by the magnet devices so that it is inversely proportional to an ion beam energy of an ion beam right be implanted.

Further adjustments of the planar Faraday cup may be executed to reflect the possible variations of the required ion beam. Of course, it also is possible to use a fixed configuration of the planar Faraday cup that is suitable for all possible variations. For example, during a maintenance period of the ion implanter, the planar Faraday cup (or the projection of the planar Faraday cup on the inner surface) may be extended along a direction across the ion beam path from the mass analyzer to the workpiece position. For example, one or more conductive plates attached on the inner surface of the chamber wall may be added or removed during a maintenance period of the ion implanter. Herein, the extended distance, or the size of the added/removed conductive plates, is inversely proportional to a predetermined low limitation of ion beam energy. For example, during a maintenance period of the ion implanter, it is optional to adjust a number, a shape and a size of one or more conductive plates integrated as the planar Faraday cup. Hence, when required ion beam is different owing to different required implantations on the workpiece, the planar Faraday cup may be pre-adjusted to reflect the potential beam expansions and deflections during the next operation period. For example, during a maintenance period of the ion implanter, the magnet device may be adjusted to ensure a magnetic field parallel to the inner surface in a section of the planar Faraday cup near the opening of the additional Faraday cup, even to change where the magnetic field turns and becomes perpendicular to the inner surface. For example, to change the used thin magnets during a maintenance period of the ion implanter, the generated magnetic field may be changed before the operation period of the ion implanter.

In summary, these proposed embodiments and other non-disclosed embodiments may efficiently receive and measure the ion beam with beam expansion, beam deflection and/or larger beam size. Hence, the practical ion beam current may be precisely real-time measured, and then the implant dose control may be improved. Further, the thickness of the proposed planar Faraday cup and the proposed magnet device is small, and the profiler may be skipped and not used. Hence, the proposed apparatus may be achieved simplify without significantly modifying the chamber.

Although the present invention has been explained in relation to its preferred embodiments, it is to be understood that other modifications and variation can be made without departing from the spirit and scope of the invention as hereafter claimed.

What is claimed is:

1. An ion beam current measurement apparatus, comprising:
   a planar Faraday cup being located close to an inner surface of a chamber wall and facing an inner space of a chamber;

a magnet device being located close to said planar Faraday cup; and an additional Faraday cup being a deep structure that extends into said chamber wall and having an opening that faces said inner space, wherein said planar Faraday cup surrounds said opening.

2. The apparatus as set forth in claim 1, said planar Faraday cup and said chamber wall being configured according to at least one of the following:

said planar Faraday cup having a non-zero angle with respect to said chamber wall;

said planar Faraday cup is essentially parallel to said inner surface of said chamber wall; and said planar Faraday cup is absolutely parallel to said inner surface of said chamber wall.

3. The apparatus as set forth in claim 1, said planar Faraday cup consisting of one or more conductive plates, wherein each said conductive plate is electrically insulated with other said conductive plates.

4. The apparatus as set forth in claim 3, both a number and a configuration of said conductive plates being flexible, wherein said configuration includes at least a size, a shape and a position.

5. The apparatus as set forth in claim 1, a material of a surface of said planar Faraday cup being chosen from a group consisting of the following: graphite, conductive glue, conductive film, and so on.

6. The apparatus as set forth in claim 1, said magnet device being located between said planar Faraday cup and said chamber wall.

7. The apparatus as set forth in claim 3, said magnet device consisting of one or more thin magnets that correspond to said conductive plates in a one-on-one relation.

8. The apparatus as set forth in claim 1, said magnet device being configured and powered to adequately suppress a secondary electron and an incoming electron as well as a low energy ion.

9. The apparatus as set forth in claim 3, further comprising one or more current meters, said current meters being electrically connected to said conductive plates in a one-on-one relation.

10. The apparatus as set forth in claim 1, said planar Faraday cup being configured according to at least one of the following:

said planar Faraday cup covering an entire area around said opening without any gap; and said planar Faraday cup being extended, wherein a projection of an extended distance on said inner surface is inversely proportional to a predetermined low limitation of an ion beam energy.

11. The apparatus as set forth in claim 1, said magnet device being designed so that a magnetic field is parallel to said inner surface in a section of said planar Faraday cup near said opening.

12. The apparatus as set forth in claim 1, further comprising one or more additional conductive plates perpendicular to said planar Faraday cup at an entrance of said opening, said additional conductive plates being electrically floating and electrically connected to said planar Faraday cup.

13. The apparatus as set forth in claim 12, wherein said planar Faraday cup is consisting of one or more conductive plates, said additional conductive plates corresponding to said conductive plates in a one-on-one relation.

14. A method for measuring ion beam current, comprising:

preparing an ion beam current measurement apparatus in an ion implanter, said ion beam current measurement apparatus comprising a planar Faraday cup being located close to an inner surface of a chamber wall and facing an inner space of said chamber, and a magnet device being located close to said planar Faraday cup;

monitoring an ion beam current appeared on said planar Faraday cup; and surrounding said planar Faraday cup around an opening of an additional Faraday cup, wherein said additional Faraday cup is a deep structure extending into said chamber wall and said opening faces said inner space.

15. The method as set forth in claim 14, comprising at least one of the following:

adjusting said magnet device during a maintenance period of said ion implanter, wherein said adjustment ensures a magnetic field parallel to said inner surface in a section of said planar Faraday cup near said opening; and locating one or more additional conductive plates perpendicular to said planar Faraday cup at an entrance of said opening, said additional conductive plates being electrically floating and connected to said planar Faraday cup.

16. The method as set forth in claim 14, further comprising adjusting a magnetic field generated by said magnet device during an operation period of said ion implanter, wherein an amplitude of said magnetic field is inversely proportional to an ion beam energy of an ion beam right be implanted.

17. The method as set forth in claim 14, further comprising extending a projection of said planar Faraday cup on said inner surface during a maintenance period of said ion implanter, wherein an extended distance is inversely proportional to a predetermined low limitation of an ion beam energy.

18. The method as set forth in claim 14, further comprising adjusting a number, a shape and a size of one or more conductive plates integrated as said planar Faraday cup during a maintenance period of said ion implanter.

* * * * *